United States Patent
Garcia De Castro Andrews

(10) Patent No.: US 8,465,448 B2
(45) Date of Patent: Jun. 18, 2013

(54) DEVICES FOR THE ADMINISTRATION OF DRUGS AND VACCINES IN THE FORM OF INJECTABLE NEEDLES

(75) Inventor: Arcadio Garcia De Castro Andrews, Madrid (ES)

(73) Assignee: Azurebio S.L. (ES)

( * ) Notice: Subject to any disclaimer, the term of this patent is extended or adjusted under 35 U.S.C. 154(b) by 98 days.

(21) Appl. No.: 12/867,957

(22) PCT Filed: Feb. 18, 2009

(86) PCT No.: PCT/EP2009/001157
§ 371 (c)(1),
(2), (4) Date: Oct. 29, 2010

(87) PCT Pub. No.: WO2009/103513
PCT Pub. Date: Aug. 27, 2009

(65) Prior Publication Data
US 2011/0040245 A1    Feb. 17, 2011

(30) Foreign Application Priority Data
Feb. 18, 2008 (ES) .................................. 200800432

(51) Int. Cl.
*A61M 31/00* (2006.01)
*A61M 5/00* (2006.01)
*A61M 5/32* (2006.01)

(52) U.S. Cl.
USPC .............................. 604/60; 604/110; 604/198

(58) Field of Classification Search
USPC ......................... 604/110, 58, 59–64, 192–198
See application file for complete search history.

(56) References Cited

U.S. PATENT DOCUMENTS

| 5,273,532 | A | * | 12/1993 | Niezink et al. | 604/62 |
| 5,542,920 | A | * | 8/1996 | Cherif Cheikh | 604/57 |
| 5,681,291 | A | | 10/1997 | Galli | 604/192 |
| 6,102,896 | A | | 8/2000 | Roser | 604/218 |
| 7,252,686 | B2 | * | 8/2007 | Carrison et al. | 623/17.16 |
| 7,615,234 | B2 | * | 11/2009 | Potter et al. | 424/426 |
| 7,976,489 | B2 | * | 7/2011 | Lawter et al. | 604/63 |
| 7,976,491 | B2 | * | 7/2011 | Lawter et al. | 604/63 |
| 2003/0054044 | A1 | | 3/2003 | Potter et al. | 424/489 |

FOREIGN PATENT DOCUMENTS
GB    2 190 590    11/1987

* cited by examiner

*Primary Examiner* — Matthew F Desanto
(74) *Attorney, Agent, or Firm* — Ostrolenk Faber LLP

(57) ABSTRACT

The present disclosure refers to hand operated disposable devices for the administration of drugs, vaccines and other medicaments in the form of solid injectable needles. The devices incorporate mechanisms for the automatic retraction of the injection rod even when the user continues to exert pressure on the device. The devices can incorporate an injectable needle in a sheath or cartridge that facilitates its manufacture and manipulation. These injection devices can only be used once and their use results in a change of configuration that renders them non operational and prevents contact with parts that have been exposed to the patient's tissues.

22 Claims, 4 Drawing Sheets

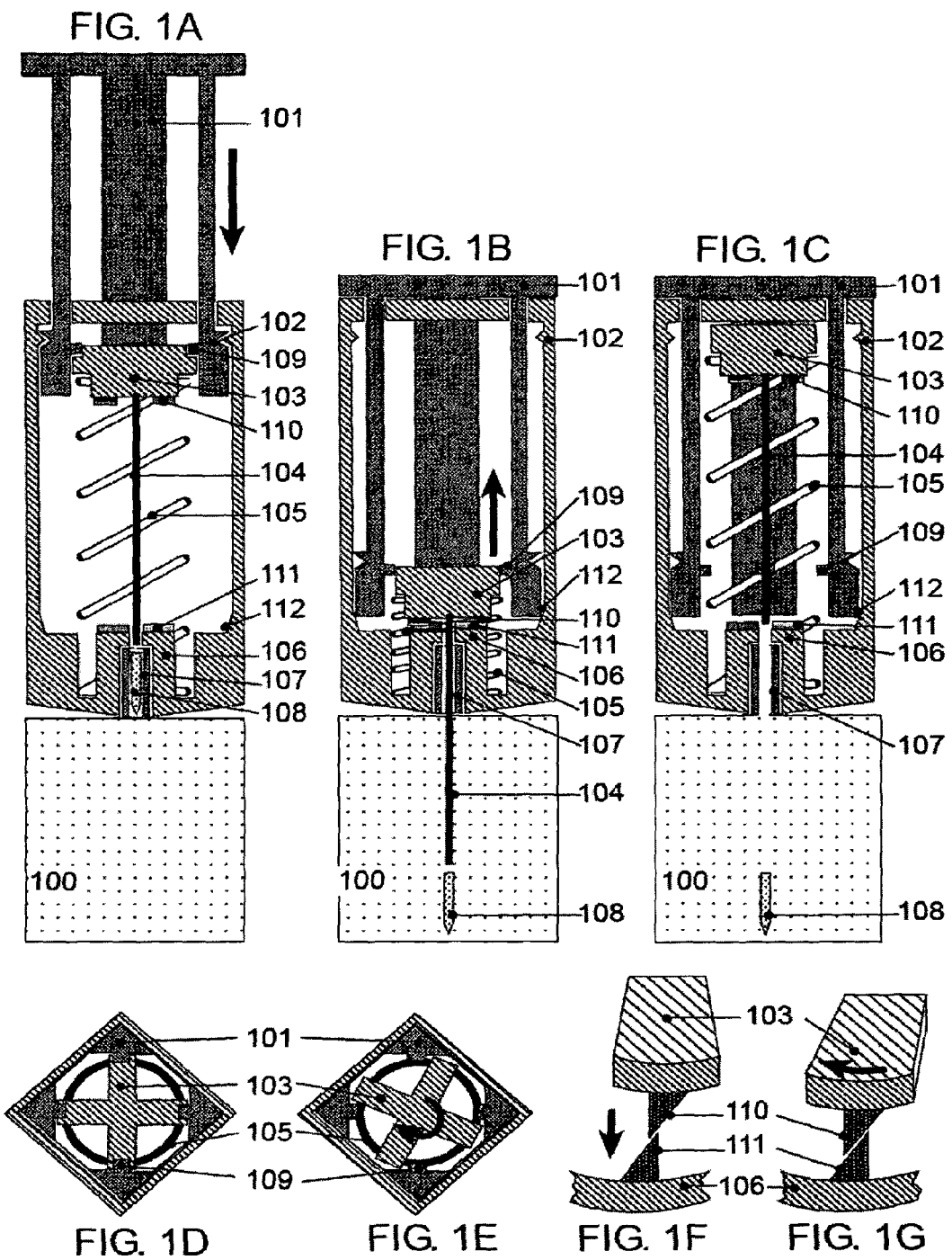

FIG. 2A
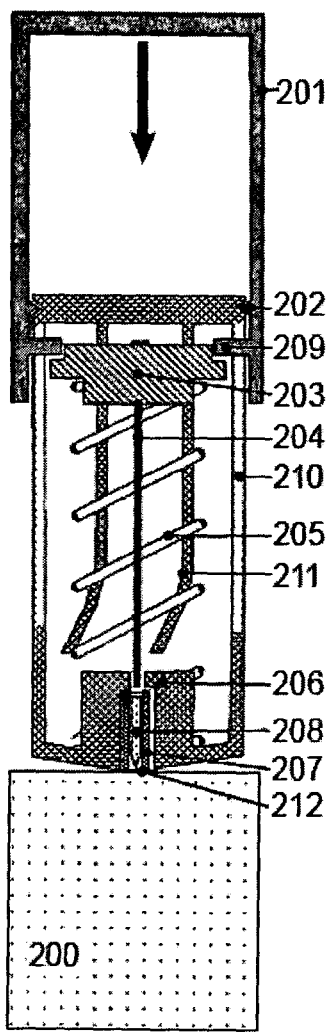
FIG. 2B
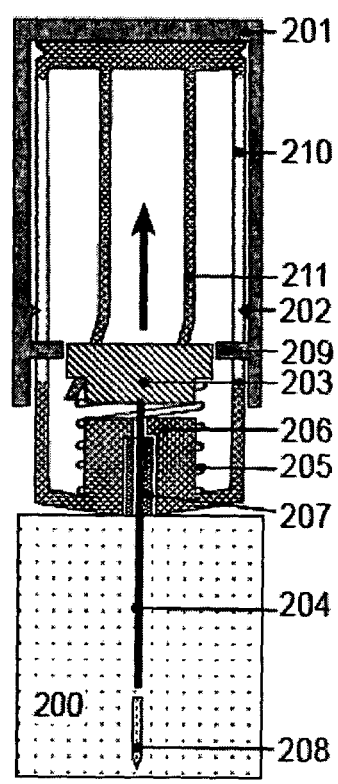
FIG. 2C
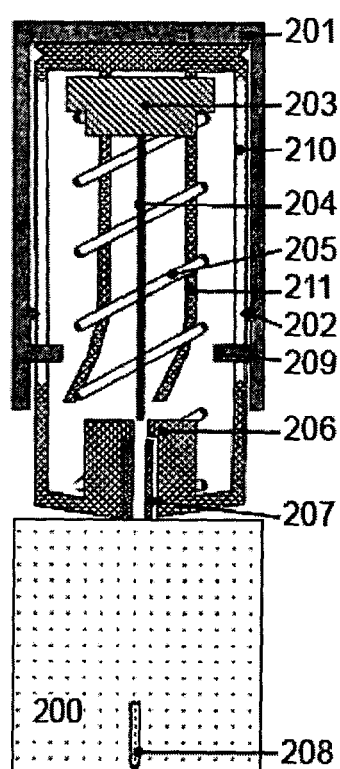
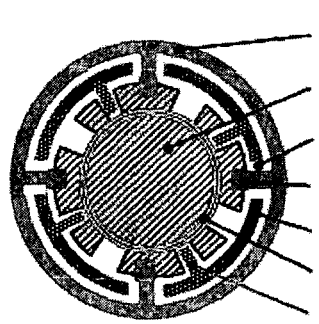
FIG. 2D
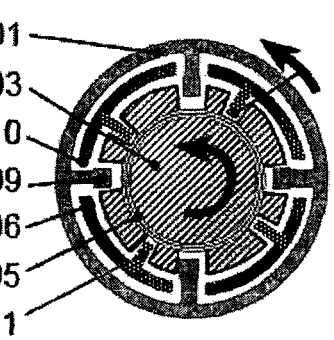
FIG. 2E
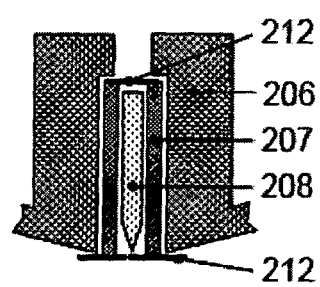
FIG. 2F

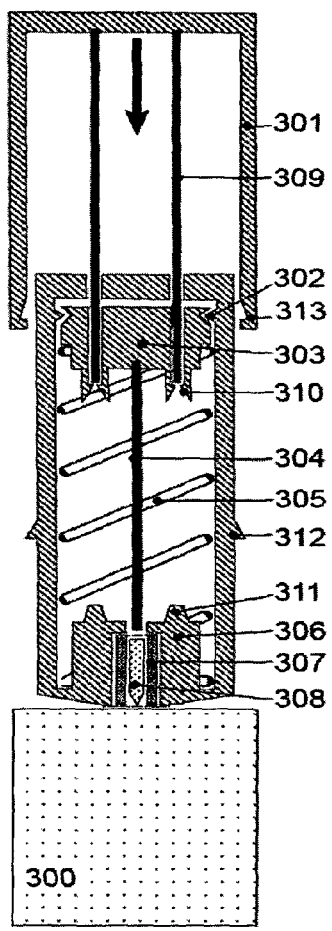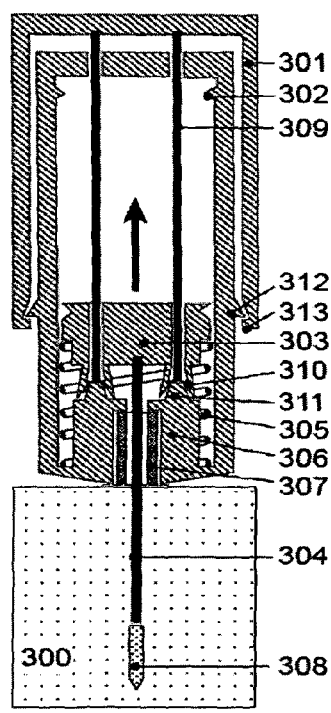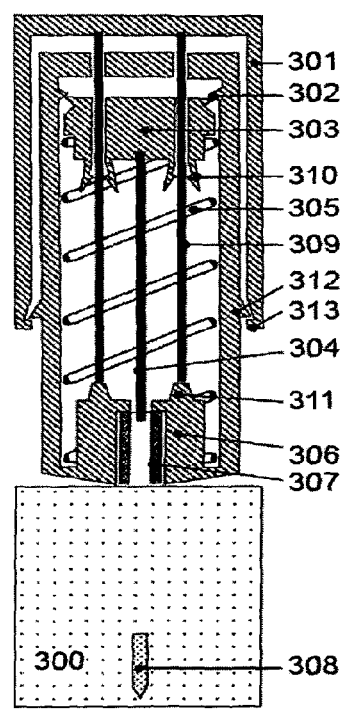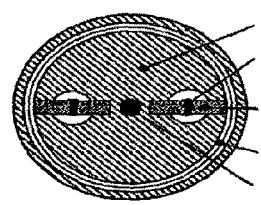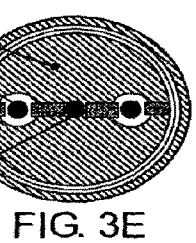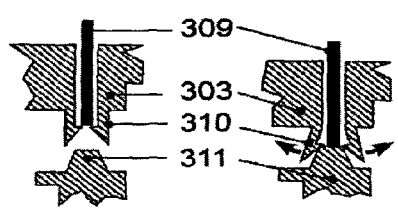

DEVICES FOR THE ADMINISTRATION OF DRUGS AND VACCINES IN THE FORM OF INJECTABLE NEEDLES

CROSS REFERENCE TO RELATED APPLICATIONS

The present application is a 35 U.S.C. §371 National Phase conversion of PCT/EP2009/001157, filed Feb. 18, 2009, which claims benefit of Spanish Application No. P200800432, filed Feb. 18, 2008, the disclosure of which is incorporated herein by reference. The PCT International Application was published in the English language.

FIELD OF INVENTION

The invention refers to hand operated disposable devices for the administration of drugs and vaccines in the form of solid injectable needles. The devices are an alternative to conventional needle and syringe devices, and avoid the need for reconstitution, refrigeration and trained personnel in the administration of drugs and vaccines.

BACKGROUND

Many drugs and vaccines are administered parenterally by means of injection by medically trained personnel. This involves a first step of reconstitution of the medicament with sterile water for injection, a second step for loading a syringe with an appropriate volume of the dissolved drug, a third step for assembling a sterile needle for injection, a fourth step of administration to the patient by injection, and a final step for safe disposal of the used device. This injection process can be problematic, especially in geographic locations with limited resources. In particular many medicaments require refrigeration in their transport and storage, and failure in maintaining the cold chain can result in significant wastage. More so, the need for reconstitution with sterile water can also be a problem in cases of microbial contamination or use of incorrect reconstitution volumes. Furthermore, the reuse of syringes and needles represents a serious global health problem due to the potential transmission of infectious agents such as Hepatitis or HIV. These problems are specially acute in the administration of vaccines in the developing world, where the World Health Organisation has for long recognised the need for alternative methods (Jodar L. et al. 1998. Revolutionising Immunisations. Gen. Eng. News 18-4).

An alternative method proposed in the administration of medicaments incorporates the administration of solid injectable needles with enough strength and hardness that permits their injection. Once these needles are injected they dissolve or degrade to liberate the medicament. Examples of these injectable needles are illustrated in WO/03023773, and U.S. Pat. No. 6,102,896. If formulated appropriately, injectable needles should avoid the need for refrigeration, reconstitution and use of conventional stainless steel hypodermic needles in the administration of medicaments.

The administration of medicaments in the form of solid injectable needles requires the appropriate devices. Examples of these include those proposed in U.S. Pat. No. 5,542,920 that describes simple devices for the administration of injectable needles which have a sharp tip and are hard enough to penetrate the skin. More so, U.S. Pat. No. 6,102,896 describes an injector for the administration of injectable needles that incorporates breakable tabs that facilitate injection. Injection of injectable needles by means of the devices described in the preceding documents is carried out by direct manual compression action by the user over an actuator. These devices have the inconvenient that the retraction of the injection rod requires the user to liberate the device from the pressure used for the injection, or the removal of the device from immediate contact with the skin. This can result in the injection rod remaining in the body for longer than required and undesirable pain. More so, these devices can be reused or result in accidental third party contamination through accidental contact with the injection rod which has penetrated the patients skin. Furthermore, none of these documents describes methods or designs that facilitate loading the injectable needles into the injectors.

More recently, WO/03023773 proposes injectable needles composed of a solid soluble tip followed by the medicament in the form of a liquid, a paste or a solid. The devices described incorporate a disposable head section and a reusable body. In these devices the user loads the device by means of extending the device and compression of an internal spring. Triggering the device results in the extension of the spring and impact of a piston with another piston attached to the injection rod which pushes forward the injectable needle containing the medicament. The device incorporates a simple mechanism that allows for a small retraction of the injection rod and in its realisation it describes that the injection rod penetrates the skin just enough for the injectable needle to cross the superficial skin. One limitation of the design is that the injectable needles cannot be injected at any significant depth. This can be a serious problem in the administration of medicaments that require a greater injection depth as is the case for most vaccines with optimum depths between 10 mm and 25 mm. Furthermore, the invention focuses on complex devices that can be reused by means of exchangeable head pieces but that presumably have a high economic cost.

In general, previous designs do not allow for simple disposable devices that permit a deep injection and the automatic retraction of the injection rod, to provide efficacious rapid and painless injection while avoiding possible reutilisation of the device and possible third party infection through accidental contact with the injection rod.

It is therefore desirable to have simple disposable devices for the injection of injectable needles containing a medicament at the required depth and that, a) facilitate the manufacture and loading of the injectable needle into the injection device, b) have a mechanism that results in a rapid entry and retraction of the injection rod that pushes forward the injectable needle, and c) that incorporate mechanisms that avoid their reuse and risk of third party contamination.

SUMMARY

The administration of medicaments in the form of injectable needles by means of simple devices avoids the need for trained personnel, cold chain, reconstitution with water for injection, and possible reuse of needles and syringes. This is of particular interest in human health, especially in the developing world or in situations that require self administration of a medicament. The present invention describes simple single use disposable devices for the administration of medicaments in the form of solid injectable needles. The devices incorporate in their design mechanisms that permit the administration of injectable needles at depths up to 25 mm, the automatic retraction of the injection rod once the injection is completed, and the inactivation of the device. The devices can also be made to incorporate a sheath to contain the injectable needle and facilitate its manipulation and manufacture.

DESCRIPTION OF FIGURES

FIGS. 1A-G. Show a realisation of a device for the injection of injectable needles with a retractile injection rod that automatically retracts after rotation of an internal plunger induced by a tab.

FIGS. 1A-C depict longitudinal section views, between opposite corners of its square section, of an injection device at different times during its utilisation. FIG. 1A shows the device prior its operation by the user by exerting force on the actuator 101. FIG. 1B shows the device at the moment of maximum penetration in the skin 100 of the injection rod 104 and the injectable needle 108, rotation of the internal plunger 103, and liberation of the spring 105 to allow for the retraction of the internal plunger 103 and the injection rod 104 in the direction of the arrow. FIG. 1C depicts the final position of the different parts of the device after extension of the spring 105, retraction of the internal plunger 103 and the injection rod 104. In this position the device is disabled and ready for its disposal. FIGS. 1D-E show different views of transversal sections of the device at the level of the tabs 109. FIG. 1D shows the position of the tabs 109 and the internal plunger 103 before the utilisation of the device as is depicted in FIG. 1A. FIG. 1E shows the point of maximum penetration of the injection rod 104 represented by FIG. 1B, at which point the internal plunger 103 rotates in the direction shown by the arrow and is liberated from the tabs 109.

FIGS. 1F-G shows the arrangement of the internal plunger 103, the body of the injector 106, and the arrangement of the tabs 110 and 111. FIG. 1F shows the moment immediately before the interaction of the tabs 110 and 111 which have an oblique vertical section. The arrow indicates the direction of the vertical movement of the internal plunger 103. FIG. 1G depicts the rotation mechanism of the internal plunger 103 in the direction of the arrow induced by the descending movement of the internal plunger 103 and interaction of tabs 110 and 111 at the moment of maximum penetration of the injection rod 104 represented in FIG. 1B.

FIGS. 2A-F. Show a realisation of a device for the injection of injectable needles with a retractile injection rod that automatically retracts after rotation of an internal plunger induced by guides.

FIGS. 2A-C depict longitudinal section views, coinciding with the tabs 209, of an injection device at different times during its utilisation.

FIG. 2A shows the device prior its operation by the user by exerting force on the actuator 201. FIG. 2B shows the device at the moment of maximum penetration in the skin 200 of the injection rod 204 and the injectable needle 208, rotation of the internal plunger 203, and liberation of the spring 205 to allow for the retraction of the internal plunger 203 and the injection rod 204 in the direction of the arrow. FIG. 2C depicts the final position of the different parts of the device after extension of the spring 205, retraction of the internal plunger 203 and the injection rod 204. In this position the device is disabled and ready for its disposal. FIGS. 2D-E depict transversal sections of the device at the level of the tabs 209, showing the internal plunger 203, the guides 211 and the longitudinal apertures 210 in the body 206 of the injector. FIG. 2D shows a transversal section of the device prior its utilisation as is shown in FIG. 2A, and the arrangement of the tabs 209 against the internal plunger 203. FIG. 2E shows the point of maximum penetration of the injection rod 204 represented by FIG. 2B, at which point the internal plunger 203 is forced to rotate by the guides 211 in the direction shown by the arrow and is liberated from the tabs 209. FIG. 2F shows a longitudinal section of the injector body 206 that incorporates a tubular sheath 207 and septa 212 covering the injectable needle 208.

FIGS. 3A-F. Show a realisation of a device for the injection of injectable needles with a retractile injection rod that automatically retracts after the deformation of tabs.

FIGS. 3A-C depict longitudinal section views of an injection device at different times during its utilisation. FIG. 3A shows the device prior its operation by the user by exerting force on the actuator 301. FIG. 3B shows the device at the moment of maximum penetration in the skin 300 of the injection rod 304 and the injectable needle 308, deformation or rupture of tabs 310, and liberation of the spring 305 to allow for the retraction of the internal plunger 303 and the injection rod 304 in the direction of the arrow.

FIG. 3C shows the final position of the different parts of the device after extension of the spring 305, retraction of the internal plunger 303 and the injection rod 304. In this position the device is disabled and ready for its disposal.

FIGS. 3D-E depict transversal sections of the device at the level of the tabs 310, showing the internal plunger 303, the rods 309, the tabs 310 and spring 305. FIG. 3D shows the device prior its utilisation as is shown in FIG. 3A, and the arrangement of the tabs 310 preventing the retraction of the internal plunger 303. FIG. 3E shows the point of maximum penetration of the injection rod 304 represented by FIG. 3B, at which point the tabs 310 are broken or deformed, liberating the rods 309 and permitting the automatic retraction of the internal plunger 303 by the action of the spring 305.

FIGS. 3F-G show longitudinal sections of the device at the level of tabs 310. FIG. 3F shows the arrangement of the tabs 310 and the wedges 311 prior utilisation of the device as is shown in FIGS. 3A and 3D. FIG. 3G shows the arrangement of tabs 310 and wedges 311 at the point of maximum penetration of the injection rod 304, as depicted in FIGS. 3B and 3E. At this moment the tabs 310 come into contact with the wedges 311 and are broken or deformed in the direction of the arrows, liberating the rods 309 and permitting the retraction of the internal plunger 303.

FIGS. 4A-C depict longitudinal section views of an injection device at different times during its utilisation. FIG. 4A shows the device prior its operation by the user by exerting force on the actuator 401. FIG. 4B shows the device at the moment of maximum penetration in the skin 400 of the injection rod 404 and the injectable needle 408, deformation of the apertures 410 induced by the conical shape elevation 411, and liberation of the internal plunger 403 from the tabs 409. The direction of the arrow indicates the retraction movement induced by the spring 405 over the internal plunger 403 and the injection rod 404 once these are liberated from the tabs 409. FIG. 4C shows the final position of the different parts of the device after extension of the spring 405, retraction of the internal plunger 403 and the injection rod 404. In this position the device is disabled and ready for its disposal.

FIGS. 4D-E depict transversal sections of the device at the level of the tabs 409 showing the internal plunger 403, the actuator 401, the tabs 409 and the apertures 410. FIG. 4D shows the device prior its utilisation as is shown in FIG. 4A, and the arrangement of the tabs 409 preventing the retraction of the internal plunger 203. FIG. 4E shows the point of maximum penetration of the injection rod 404 represented by FIG. 4B, at which point the elevation 411 causes the apertures 410 of the actuator 401 to deform and open, liberating the internal piston 403 from the tabs 409.

DETAILED DESCRIPTION

Figure 4A:
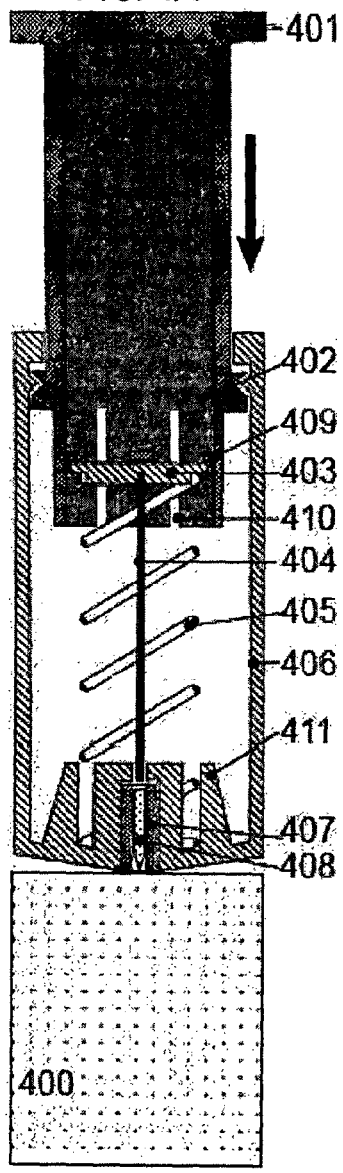
FIGS. 4A-E. Show a realisation of a device for the injection of injectable needles with a retractile injection rod that automatically retracts by means of apertures in the actuator.

The present invention incorporates simple single-use disposable devices for the administration of medicaments in the form of injectable needles at a depth up to 25 mm. The injectable needles administered with these devices are made to incorporate a medicament, are solid and hard enough to cross the skin. These needles can be formulated from amorphous or crystalline solids and can be made to be more or less soluble. The injectable needles have a diameter to length ratio between 1:15 and 1:5, a diameter between 0.2 mm and 1 mm, and a length between 1 mm and 10 mm.

The devices are operated manually by compression in direct contact with the skin, and incorporate simple mechanisms for the automatic retraction of the injection rod that pushes the injectable needle. The automatic retraction of the injection rod originates a rapid and controlled exit of the injection rod even when the user continues to put pressure on the device actuator. This avoids the injector rod from being inside the patient's body for longer than is strictly necessary. More so, these mechanisms provide with devices that are rendered useless after their use and avoid possible third party contact with parts of the device that have been in direct contact with the patient's tissues. The ease in their operation facilitates the administration by untrained personnel and self administration of medicaments formulated as solid injectable needles The devices of the present invention, as illustrated with out limitation in FIGS. 1A-G, 2A-F, 3A-G y 4A-E, incorporate an actuator 101, 201, 301 or 401 which receives the direct pressure exerted by the user to permit the advance of the internal plunger 103, 203, 303 or 403 on which the injector rod 104, 204, 304 or 404 is mounted. The injectable needle 108, 208, 308 or 408 is forced forward by the injector rod 104, 204, 304 or 404 into the patients tissues 100, 200, 300 or 400 to a depth up to 25 mm. The devices contain a spring 105, 205, 305 or 405 that is compressed as the internal plunger 103, 203, 303, or 403 is forced to advance. Once the injection is completed, the compressed spring forces the retraction of the injection rod 104, 204, 304 or 404. In a realisation of the present invention shown in FIGS. 1A-G the plunger 101 transmits the force exerted by the user to the internal plunger 103 by means of tabs 109. Once the internal plunger 103 has traveled to the end of its path, it is liberated from the tabs 109 by a rotation movement of the internal plunger 103 forced by tabs with an oblique vertical section 110 y 111. The liberation of the internal plunger 103 results in the extension of the spring 105, the rapid retraction of the internal plunger 103 and the injection rod 104. In its final position after use, the injector is deactivated and the injector rod is located hidden within the body of the injector. In this realisation, the square section of the injector permits the advance of the actuator 101 at the corners at the same time as the device provides lateral support to the spring 105 during its compression.

In another embodiment of the present invention illustrated in FIGS. 2A-F an actuator 201 located concentrically outside the body 206 of the injector transmits the force exerted by the user to the internal plunger 203 by means of tabs 209 that come through the body 206 of the injector through longitudinal apertures 210. Once the internal plunger 203 has traveled to the end of its path, it is freed from the tabs 209 by a rotating movement of the internal plunger forced by the guides 211 on the body 206 of the injector. This release of the internal plunger 203 from the tabs 209 permits the extension of the spring 205, and originates in the rapid retraction of the internal plunger 203 and the injection rod 204. In the final position after use, the injector is deactivated and the injector rod 204 located within the body 206 of the injector.

In another embodiment of the present invention shown in FIGS. 3A-G, the actuator 301 transmits the force exerted by the user to the internal plunger by means of rods 309 that come through the internal plunger 303 and are hooked to it by deformable tabs 310. Once the internal plunger 303 has traveled to the end of is path, the tabs are deformed laterally or broken by the action of a wedge 311 located on the body of the injector. This results in the release of the internal plunger 303, the extension of the spring 305 and retraction of the internal plunger and injector rod 304. In the final position after use, the injector is deactivated and the injector rod 304 located within the body 306 of the injector.

Figure 4B:
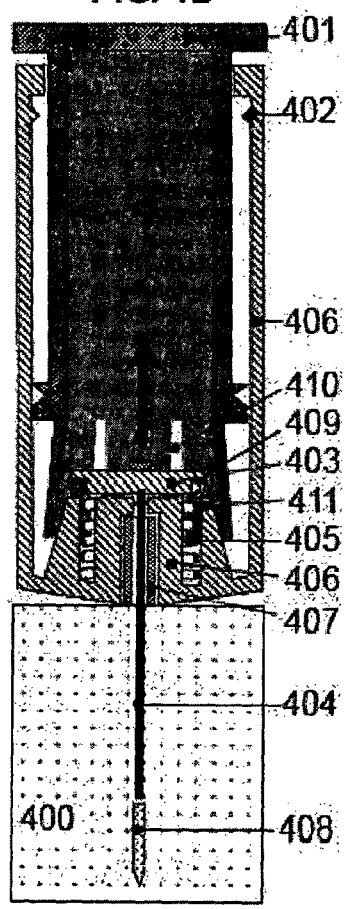
Figure 4C:
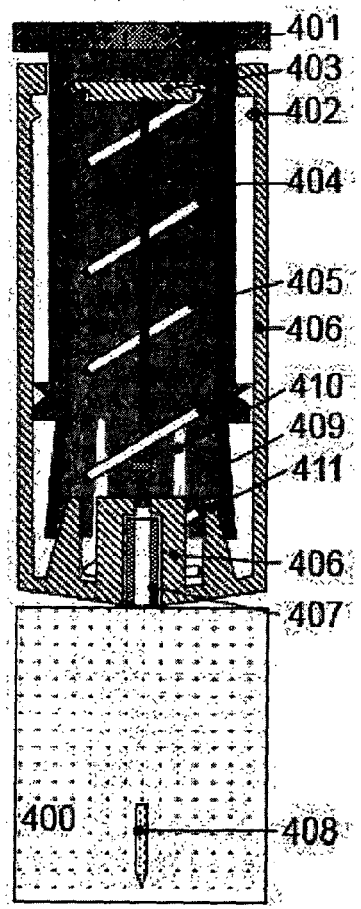
Figure 4D:
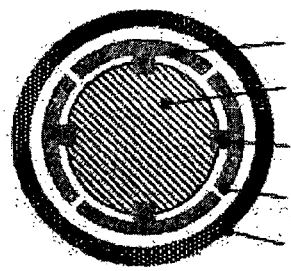
Figure 4E:
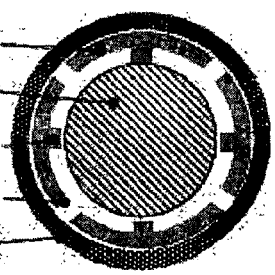

Yet in another embodiment of the present invention illustrated in FIGS. 4A-E, the internal piston 403 is freed from the tabs 409 and the actuator 401 by deformation of the apertures 410. The deformation of these apertures 410 is caused by the interaction of the actuator 401 and the conical protrusion 411 at the end of the path taken by the internal plunger 403. Liberation of the internal plunger 403 from the tabs 409 permits the extension of the spring 405 originating the rapid retraction of the internal plunger 403 and the injector rod 404. At its final position after use, the injector is deactivated and the injector rod 404 hidden within the body of the injector 406.

In another preferred embodiment of the present invention the devices can incorporate tabs 102, 202 302 or 402 that block the device prior to use and prevent the movement of the actuator 101, 201, 301 or 401 until the user exerts sufficient manual pressure.

Furthermore, in another embodiment of the present invention, the devices can incorporate a sheath 107, 207, 307 or 407 that contains the injectable needle 108, 208, 308 or 408. In one embodiment of the present invention the sheath 107, 207, 307 or 407 serves as a mould in the manufacture of the injectable needle 108, 208, 308 or 408. This can facilitate the incorporation of the injectable needle 108, 208, 308 or 408 to the device in its final assembly during manufacture. More so, the sheath can incorporate septa 212 that keep the injectable needle 108, 208, 308 or 408 within the sheath 107, 207, 307 or 407 prior to the device being used, and that are pierced by the injector at the time of injection.

Devices as those described in the present invention permit the injection of injectable needles containing medicaments as is illustrated, with out limitation, in the following examples. The devices are preloaded and simple to use by an unskilled operator exerting hand pressure on the device. The use of these devices preloaded with drugs, vaccines and other medicaments is of special interest in the developing world.

EXAMPLE 1

Injection of Injectable Needles Made from Calcium Salts by Means of an Injector that Incorporates Mechanisms for the Automatic Retraction of the Injection Rod and Inactivation of the Device A prototype as represented in FIGS. 1A-G was loaded with an injectable needle based on a cement mixture resulting from the reaction of 0.7 g of tetracalcium phosphate [$Ca_4PO_4O_2$] and 1.8 g of calcium hydrogenphosphate [$CaHPO_4$], in 1 ml of a 0.5 M of de disodium hydrogen phosphate [$Na_2HPO_4$]. The mixture was made to contain crystal violet as a model medicament. Prior to hardening, the mixture is introduced in Teflon tube with 0.4 mm internal diameter and 1.57 mm external diameter, which is used as a mould and the mix is pressed lightly with a concave piston to conform a sharp point.

Following this, the hardened needle container within the mould was introduced in a 1.57 mm orifice on the head of the injector device. Operation of the injector permitted the injection of the injectable needle in a model human tissue up to a depth of 25 mm.

What is claimed is:

1. An injector device for the injection of a solid injectable needle containing a medicament into animal or human tissues, the injection device comprising:
    an injection rod positioned and configured to inject the injectable needle into the tissues;
    an actuator configured to undergo direct manual compression so as to drive the injection rod; and
    means for causing automatic retraction of the injection rod upon reaching a point of maximum penetration, even under continued compression on the actuator,
    wherein the means for causing automatic retraction of the injection rod further comprises means for releasing a plunger from the actuator, rendering the injector device useless after one use.

2. The injector device according to claim 1, wherein the means for releasing the plunger comprises the actuator including tabs positioned and configured to push the plunger and means for causing the rotation of the plunger.

3. The injector device according to claim 2, wherein the means for causing the rotation of the plunger comprises tabs fixed to the plunger cooperating with tabs fixed to a body at an end of a path travelled by the plunger.

4. The injector device according to claim 3, wherein the means for causing the rotation of the plunger comprises axial guides deviated from the axial direction at an end of a path travelled by the plunger.

5. The injector device according to claim 1, further comprising a sheath positioned and configured to enclose the solid injectable needle containing the medicament.

6. The injector device according to claim 5, wherein the sheath further comprises septa positioned and configured to be broken during injection of the injectable needle.

7. The injector device according to claim 1, wherein the means for causing the automatic retraction of the injection rod comprises a spring connected to the plunger driven by the actuator.

8. The injector device according to claim 1, wherein the means for releasing the plunger comprises the actuator including rods positioned and configured to drive the plunger by actuating on tabs, the tabs being deformable upon cooperation with wedges located at an end of a path travelled by the plunger.

9. The injector device according to claim 1, wherein the means for releasing the plunger comprises the actuator including tabs positioned and configured to drive the plunger, the actuator being deformable upon cooperation with a conical protrusion located at an end of a path travelled by the plunger.

10. The injector device according to claim 1, wherein the injectable needle has a diameter:length ratio between 1:15 and 1:5, a diameter between 0.2 mm. and 1 mm., and a length between 1 mm. and 10 mm.

11. The injector device according to claim 1, wherein the injectable needle is soluble.

12. The injector device according to claim 1, wherein the injectable needle comprises calcium salts.

13. The injector device according to claim 1, further comprising a blocking tab positioned and configured to block movement of the actuator so as to prevent operation of the injector device until sufficient manual force is exerted on the actuator.

14. An injector device for the injection of an injectable needle containing a medicament into animal or human tissue, the injection device comprising:
    an injection rod positioned and configured to inject the injectable needle into the tissues;
    an actuator configured to undergo manual compression so as to drive the injection rod;
    a retractor positioned and configured to retract automatically the injection rod upon reaching a point of maximum penetration, even under continued compression on the actuator;
    a plunger positioned and configured to be driven by the actuator; and
    the retractor comprising a releaser positioned and configured to release the plunger from the actuator, rendering the injector device useless after one use.

15. The injector device according to claim 14, wherein the releaser comprises the actuator including tabs positioned and configured to push the plunger, and a rotator positioned and configured to rotate the plunger.

16. The injector device according to claim 15, wherein the rotator comprises tabs fixed to the plunger and configured to cooperate with tabs fixed to a body at an end of a path travelled by the plunger.

17. The injector device according to claim 15, wherein the rotator comprises axial guides deviated from the axial direction at an end of a path travelled by the plunger.

18. The injector device according to claim 14, wherein the retractor comprises a spring connected to the plunger driven by the actuator.

19. The injector device according to claim 14, wherein the releaser comprises the actuator including rods positioned and configured to drive the plunger by actuating on tabs deformable upon cooperation with wedges located at an end of a travel path of the plunger.

20. The injector device according to claim 14, wherein the releaser comprises the actuator including tabs positioned and configured to drive the plunger, the actuator being deformable upon cooperation with a conical protrusion located at an end of a travel path of the plunger.

21. The injector device according to claim 14, further comprising a sheath positioned and configured to enclose the injectable needle.

22. The injector device according to claim 14, further comprising a blocking tab positioned and configured to block movement of the actuator so as to prevent operation of the injector device until sufficient manual force is exerted on the actuator.

* * * * *